United States Patent
Sato

(10) Patent No.: US 10,379,037 B2
(45) Date of Patent: Aug. 13, 2019

(54) SPECTRAL COLORIMETRIC APPARATUS AND IMAGE FORMING APPARATUS THAT USES THE SAME

(71) Applicant: CANON KABUSHIKI KAISHA, Tokyo (JP)

(72) Inventor: Wataru Sato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/474,040

(22) Filed: Mar. 30, 2017

(65) Prior Publication Data

US 2017/0299504 A1    Oct. 19, 2017

(30) Foreign Application Priority Data

Apr. 14, 2016 (JP) ................ 2016-081464

(51) Int. Cl.

| | |
|---|---|
| *G01N 21/31* | (2006.01) |
| *G01N 21/86* | (2006.01) |
| *G03G 15/01* | (2006.01) |
| *B41J 2/005* | (2006.01) |
| *G03G 15/00* | (2006.01) |
| *G01J 3/02* | (2006.01) |
| *G01J 3/04* | (2006.01) |
| *G01J 3/18* | (2006.01) |
| *G01J 3/50* | (2006.01) |
| *G01J 3/52* | (2006.01) |
| *G03G 15/23* | (2006.01) |

(52) U.S. Cl.
CPC ............ *G01N 21/31* (2013.01); *B41J 2/0057* (2013.01); *G01J 3/0202* (2013.01); *G01J 3/0208* (2013.01); *G01J 3/0256* (2013.01); *G01J 3/0291* (2013.01); *G01J 3/04* (2013.01); *G01J 3/18* (2013.01); *G01J 3/50* (2013.01); *G01J 3/524* (2013.01); *G01N 21/86* (2013.01); *G03G 15/011* (2013.01); *G03G 15/5062* (2013.01); *G03G 15/234* (2013.01); *G03G 2215/00569* (2013.01)

(58) Field of Classification Search
CPC ....... G01N 21/31; G01N 21/86; G03G 15/011
USPC ......................................... 356/402
See application file for complete search history.

(56) References Cited

U.S. PATENT DOCUMENTS

| | | |
|---|---|---|
| 6,606,156 B1 | 8/2003 | Ehbets et al. |
| 8,462,406 B2 | 6/2013 | Takizawa et al. |
| 8,705,154 B2 | 4/2014 | Takizawa et al. |

(Continued)

FOREIGN PATENT DOCUMENTS

| | | |
|---|---|---|
| JP | 05-20053 U | 3/1993 |
| JP | 2000-298066 A | 10/2000 |

(Continued)

OTHER PUBLICATIONS

Abstract of Japanese Utility Model Publication No. 05-20053.

*Primary Examiner* — Hina F Ayub
(74) *Attorney, Agent, or Firm* — Venable LLP

(57) ABSTRACT

A spectral colorimetric apparatus comprises a light source, a spectral element, a light receiving element, a substrate on which the light receiving element is mounted, a housing and a pressing portion. The housing has a first side wall on which the substrate is fixed and a second side wall on which the spectral element is fixed. The pressing portion pinches the spectral element together with the second side wall and presses the spectral element to the second side wall.

35 Claims, 11 Drawing Sheets

(56) References Cited

U.S. PATENT DOCUMENTS

2010/0278543 A1* 11/2010 Takizawa .................. G01J 3/02
                                                                             399/9
2012/0105851 A1*  5/2012 Kobayashi ................ G01J 3/02
                                                                             356/402

FOREIGN PATENT DOCUMENTS

| | | |
|---|---|---|
| JP | 2010-276599 A | 12/2010 |
| JP | 2015-111130 A | 6/2015 |

* cited by examiner

F I G. 5A
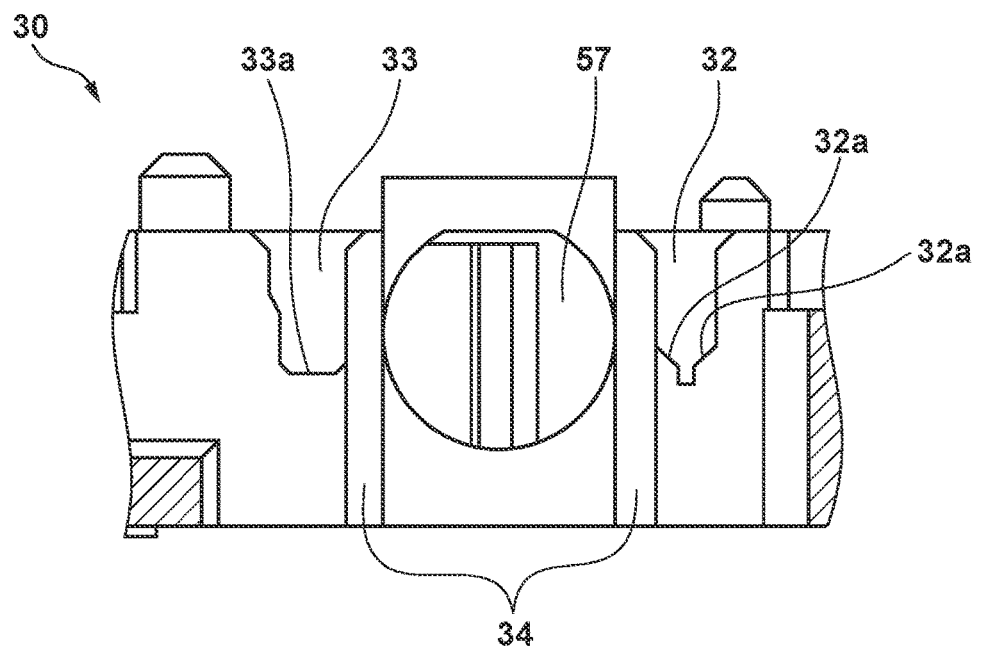
F I G. 5B
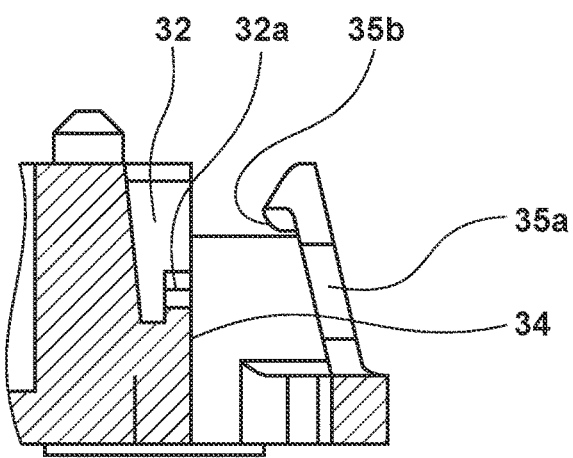

SPECTRAL COLORIMETRIC APPARATUS AND IMAGE FORMING APPARATUS THAT USES THE SAME

BACKGROUND OF THE INVENTION

Field of the Invention

The present invention relates to a spectral colorimetric apparatus and an image forming apparatus that uses the same.

Description of the Related Art

For an image forming apparatus, which forms multicolor images, to reproduce a color tone of an input image in an output image, it forms a test image on an image carrier or a sheet, that is read by a colorimetric apparatus, and a color mapping table is corrected in accordance with the read result. This sequence of processing is called calibration. Colorimetric accuracy of the colorimetric apparatus is the key to reproducing a color tone with good accuracy. By Japanese Patent Laid-Open No. 2015-111130, a fixation method of a photoelectric conversion element that contributes to a miniaturization of a colorimetric apparatus is disclosed.

By virtue of the invention recited in Japanese Patent Laid-Open No. 2015-111130, a miniaturization of a colorimetric apparatus is also realized in addition to being able to fix a photoelectric conversion element with good accuracy. However, the invention of Japanese Patent Laid-Open No. 2015-111130 has room for improvement regarding a method of fixation to a housing of a spectral optical element.

SUMMARY OF THE INVENTION

Accordingly, in the present invention, a spectral optical element can be aligned with good accuracy and a simple to assemble spectral colorimetric apparatus is provided.

The present invention provides a spectral colorimetric apparatus comprising the following elements. A light source is configured to irradiate light onto a surface to be detected. A spectral element is configured to disperse reflected light that is reflected from the surface to be detected. A light receiving element is configured to receive light dispersed by the spectral element and is mounted on a substrate. A housing has a first side wall on which the substrate is fixed and a second side wall on which the spectral element is fixed. A pressing portion is configured to pinch the spectral element together with the second side wall and to press the spectral element to the second side wall.

Further features of the present invention will become apparent from the following description of exemplary embodiments (with reference to the attached drawings).

BRIEF DESCRIPTION OF THE DRAWINGS

FIGS. 5A and 5B are views illustrating a spectral colorimetric apparatus

DESCRIPTION OF THE EMBODIMENTS

Figure 1:
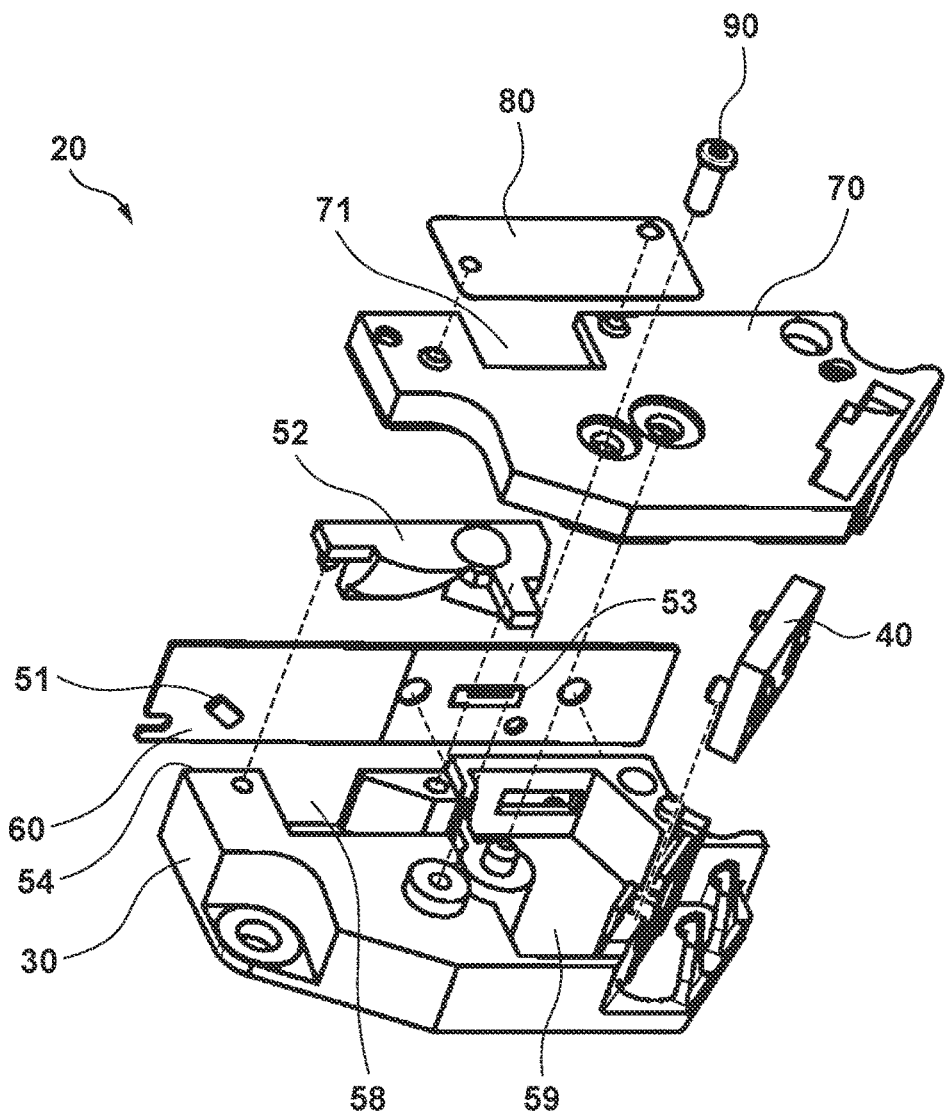
FIG. 1 is a view illustrating a spectral colorimetric apparatus
Figure 2A:
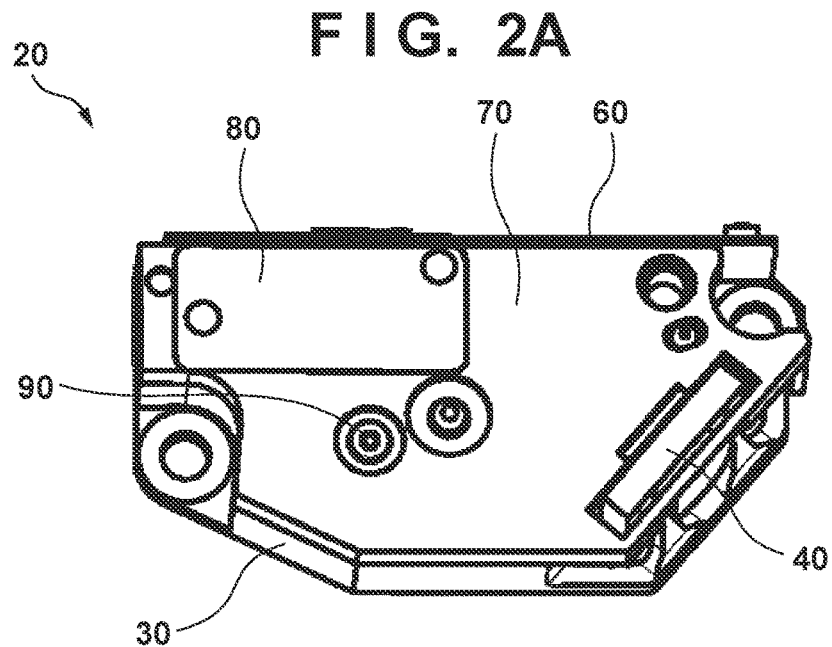
FIGS. 2A and 2B are views illustrating a spectral colorimetric apparatus
Figure 2B:
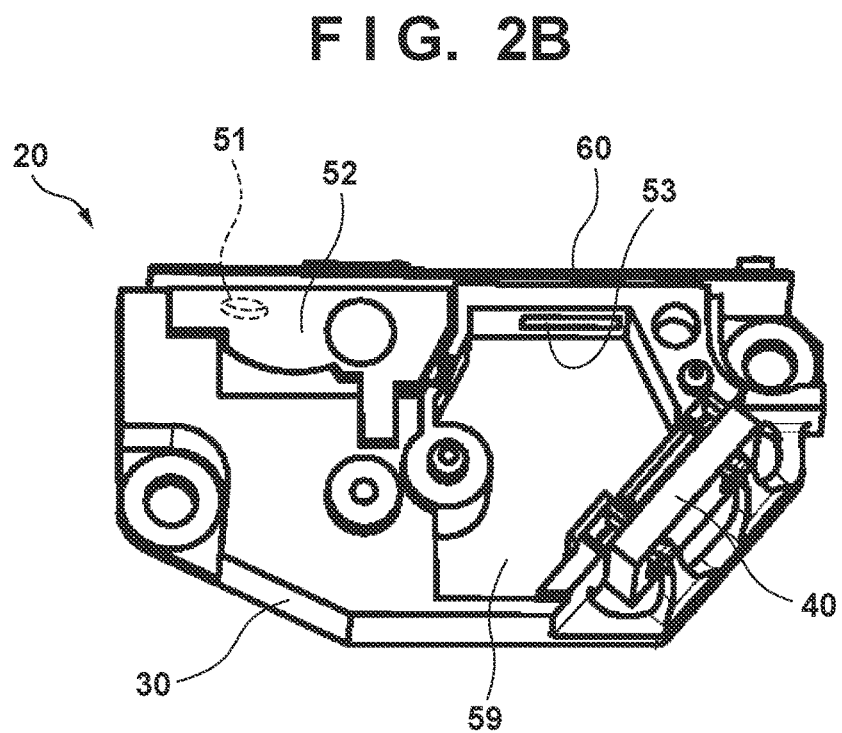

FIG. 1 is an exploded perspective view of a spectral colorimetric apparatus 20. FIG. 2A is a view illustrating an outer appearance of a spectral colorimetric apparatus 20. FIG. 2B is a view illustrating an interior of a spectral colorimetric apparatus 20. The spectral colorimetric apparatus 20 has a housing 30, a substrate 60, a light-guiding optical element 52, a spectral optical element 40, a cover 70, and a sheet 80 as FIG. 1 illustrates. A light source 51 and a light receiving element 53 are mounted to the substrate 60. The cover 70 is a cap member and is fixed to the housing 30 by a screw 90. The housing 30 may be manufactured by plastic molding. The light-guiding optical element 52 is fixed to a predetermined position of the housing 30 by an adhesive agent or the like for example. The spectral optical element 40 is pressed by an arm portion arranged on the housing 30 and is fixed. The substrate 60 is a printed circuit board and is fixed by a screw to a first side wall 54 of the housing 30. Note, the external surface of the first side wall 54 (outside wall surface) and a mounting surface of the substrate 60 are opposing. The cover 70 is attached parallel to the bottom surface of the housing 30. An opening 71 through which light emitted from the light source 51 passes is arranged on the cover 70. The sheet 80 which is transparent and whose area covers the opening 71 may be affixed to the cover 70. A first space 58 accommodating the light-guiding optical element 52 and a second space 59, through which a light beam emitted from the light-guiding optical element 52 that is incident onto the spectral optical element 40 passes, are arranged on the housing 30. Note, a light beam that is dispersed by the spectral optical element 40 also passes through the second space 59 and toward the light receiving element 53.

Figure 3A:
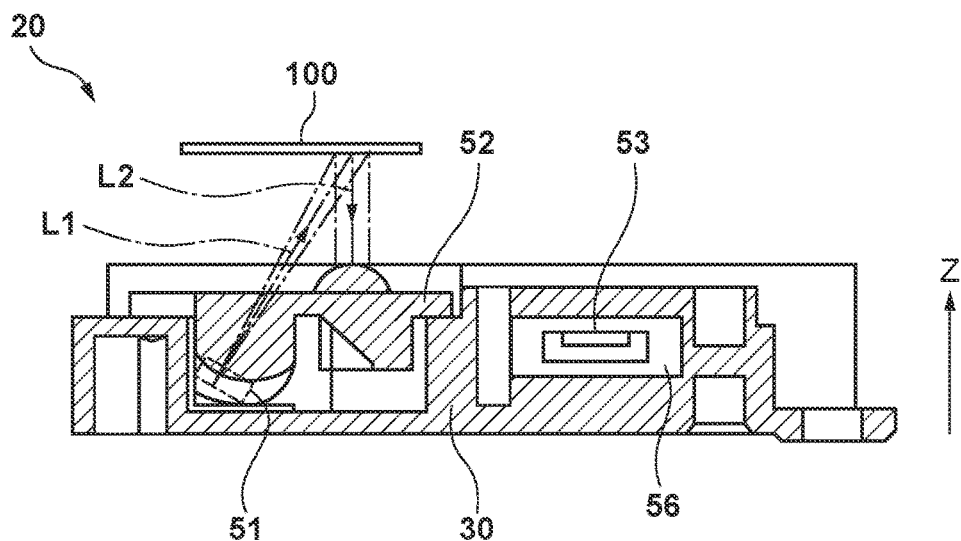
FIGS. 3A and 3B are views illustrating a spectral colorimetric apparatus
Figure 3B:
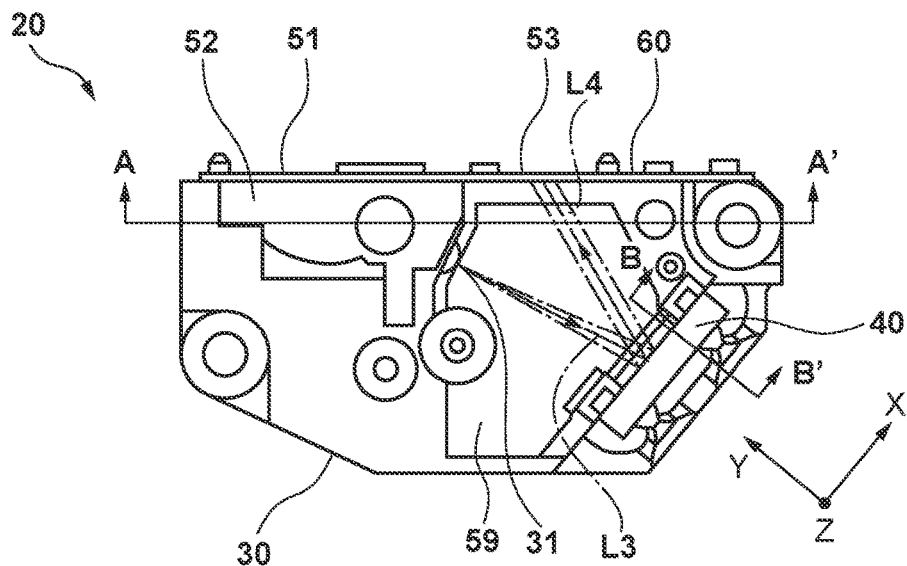

FIG. 3A is a cross-sectional view for describing the light path of the spectral colorimetric apparatus 20. A normal direction (a Z direction) of the bottom surface of the housing 30 is indicated by an arrow symbol in FIG. 3A. The normal direction may be called the height direction for convenience of description. FIG. 3B is a plan view illustrating the spectral colorimetric apparatus 20 with the cover 70 removed. Note, FIG. 3A illustrates a cross section obtained by cutting the spectral colorimetric apparatus 20 along the cut surface A-A' illustrated in FIG. 3B. A slit 31 is arranged on an inside wall dividing the first space 58 and the second space 59 as FIG. 3B illustrates. The light beam that the light-guiding optical element 52 emits enters from the first space 58 to the second space 59 through the slit 31. A detection object 100 that FIG. 3A illustrates is a sheet, an image carrier, or the like on which an image is formed for example. The detection object 100 may be conveyed parallel to the cover 70.

A light axis L1 that FIG. 3A illustrates is a light axis of the light beam emitted from the light source 51. The light beam emitted from the light source 51 reflects and refracts on the interior of the light-guiding optical element 52 and is irradiated onto the detection object 100. A light axis L2 indicates a light axis of the light beam reflected by the detection object 100. The light beam reflected by the detection object 100 re-enters the light-guiding optical element 52. The light-guiding optical element 52 has an anamorphic surface for focusing the light beam in a direction parallel to a dispersion direction of the spectral optical element 40 and a function for bending the light beam in a direction parallel to the detection object 100. By this, the light beam of the light axis L2 substantially focuses on the slit 31.

In FIG. 3B, a light axis L3 is a light axis of the light beam passing through the slit 31 which is casted integrally in the housing 30. The light beam of the light axis L3 is incident on a diffraction grating of the spectral optical element 40. The diffraction grating is a concave reflective type diffraction grating arranged on a first side (referred to as the front surface) of the spectral optical element 40. A light axis L4 is a light axis of the light beam that is reflected and dispersed by the spectral optical element 40. An opening 56 through which the light beam dispersed by the spectral optical element 40 passes may be arranged on the first side wall 54 as FIG. 3A illustrates. The light beam of the light axis L4 passes through the opening 56 and becomes a slit image that is focused on a light-receiving surface of the light receiving element 53. Note, the slit image is focused on a plurality of positions in accordance with a wavelength of the light included in the light beam because the light beam of the light axis L4 is dispersed by the spectral optical element 40.

The light receiving element 53 which receives the light beam dispersed by the spectral optical element 40 has a plurality of photoelectric conversion elements such as photodiodes lined up in a dispersion direction. The slit image that is dispersed on each photoelectric conversion element of the light receiving element 53 is focused. Each photoelectric conversion element outputs a detection signal in accordance with the intensity of the received light. A later described controller corrects the detection signal in accordance with spectral characteristics of the light source 51, spectral sensitivity characteristics of the light receiving element 53, or the like, and calculates a color tone of the image formed on the detection object 100 based on the detection signal.

An X direction is a direction in which the light beam of the light axis L3 is dispersed as FIG. 3B is illustrated. A Y direction is perpendicular to the X direction and is a direction parallel to a plane which includes the light axis L3 and the light axis L4. A Z direction illustrated in FIG. 3A is perpendicular to the X direction and the Y direction.

<Attaching Portion of the Spectral Optical Element 40>

Figure 4A:
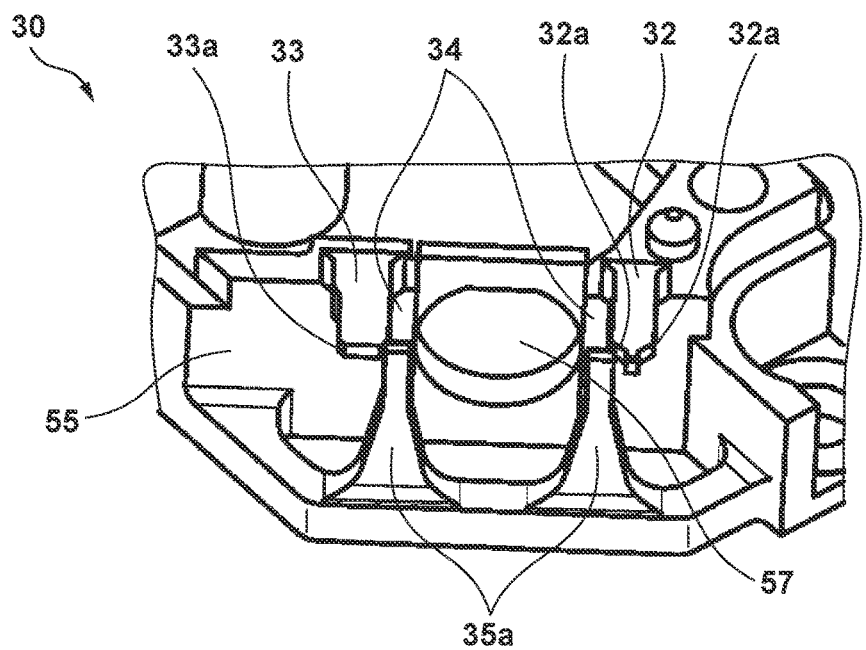
FIGS. 4A and 4B are views illustrating a spectral colorimetric apparatus
Figure 4B:
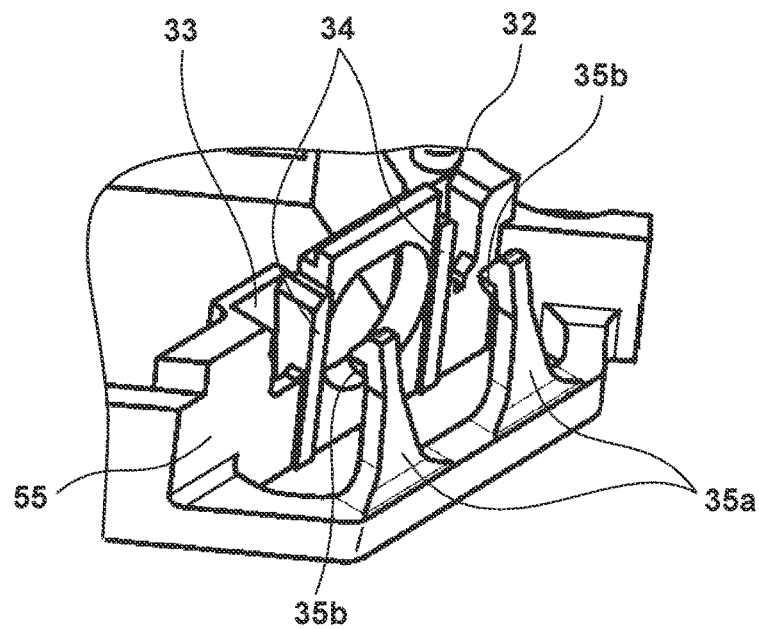

FIG. 4A and FIG. 4B are perspective views illustrating an attaching portion of the spectral optical element 40. FIG. 5A is a side view of the attaching portion. FIG. 5B is a perspective view of the attaching portion. The perspective view is a perspective view when viewing in the X direction from a cross section of the attaching portion on the B-B' line illustrated in FIG. 3B. A circular opening 57 is arranged on a second side wall 55 of the housing 30. A light beam passing through the interior of the second space 59 is directed from the opening 57 to the exterior of the second space 59. The opening 57 is arranged by alignment with a position of the diffraction grating of the spectral optical element 40.

A first groove portion 32 and a second groove portion 33 are arranged on the second side wall 55. The cross-sectional shape of the bottom portion 32a of the first groove portion 32 is V-shaped. The surface of the bottom portion 32a may be called a V-shaped surface. Although a large portion of the bottom portion 33a of the second groove portion 33 illustrated in FIG. 5A and the like is planar, the cross-sectional shape of the bottom portion 33a may be V-shaped or U-shaped. Two wall surfaces 34 are arranged in a central proximity of the second side wall 55. The two wall surfaces 34 may be slightly protruding in a direction (−Y direction) directed from the interior to the exterior of the housing 30. An arm portion 35a is a support component for fixing or supporting the spectral optical element 40. The arm portion 35a protrudes in the Z direction from the bottom surface extending further to the outside than the second side wall 55 out of the bottom surface of the housing 30. The protruding portion 35b is arranged on a leading edge of the arm portion 35a in order to press the back surface of the spectral optical element 40. Note, the arm portion 35a and the protruding portion 35b together may be called a pressing portion.

Figure 6A:
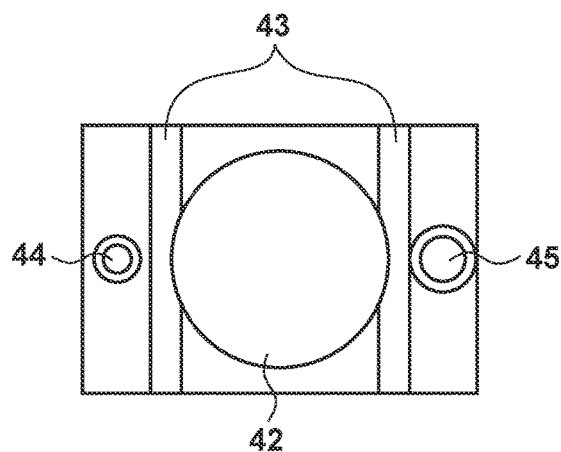
FIGS. 6A to 6D are views illustrating a spectral optical element
Figure 6B:
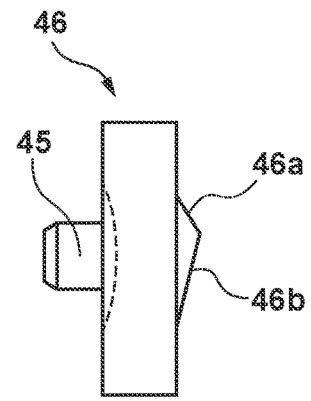
Figure 6C:
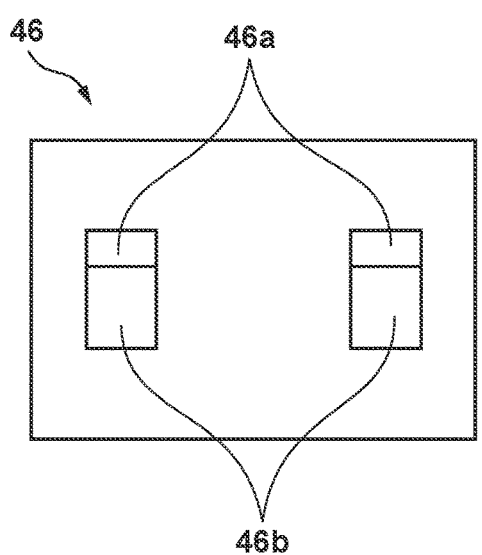
Figure 6D:
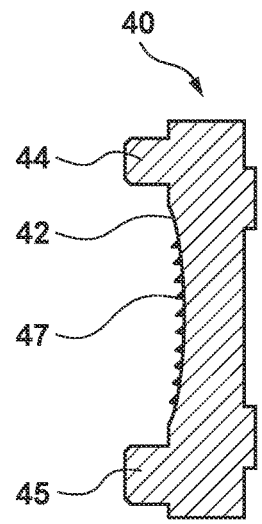

FIG. 6A is a side view (front surface view) of the spectral optical element 40 when viewing in a −Y direction from the inside of the housing 30. FIG. 6B is a side view (left side surface view) of the spectral optical element 40. FIG. 6C is a side view (back surface view) of the spectral optical element 40. FIG. 6D is a cross-sectional view of the spectral optical element 40. The cross section passes through the center of the spectral optical element 40 and is a plane that is parallel to the XY plane. A spectral reflective surface 42 is arranged in a central proximity of the spectral optical element 40 as FIG. 6A and FIG. 6D illustrate. A diffraction grating 47 of a concave shape is arranged on the spectral reflective surface 42. Wall surfaces 43 are arranged on both neighboring sides of the spectral reflective surface 42. Also, a first pin 44 and a second pin 45 for alignment are arranged at both ends of the X direction on the spectral reflective surface 42. Two guide portions 46 are arranged on the back surface of the spectral optical element 40 as FIG. 6C illustrates. The guide portions 46 are directed and protrude in the −Y direction from the back surface of the spectral optical element 40. The guide portions 46 have an inclined surface 46a and an inclined surface 46b as FIG. 6C illustrates. The inclined surface 46a advances in the −Z direction as it protrudes in the −Y direction. The inclined surface 46b advances in the +Z direction as it protrudes in the −Y direction. In other words, the height of the connecting portions is highest when viewing the inclined surface 46a and the inclined surface 46b from the back surface of the spectral optical element 40.

Figure 7A:
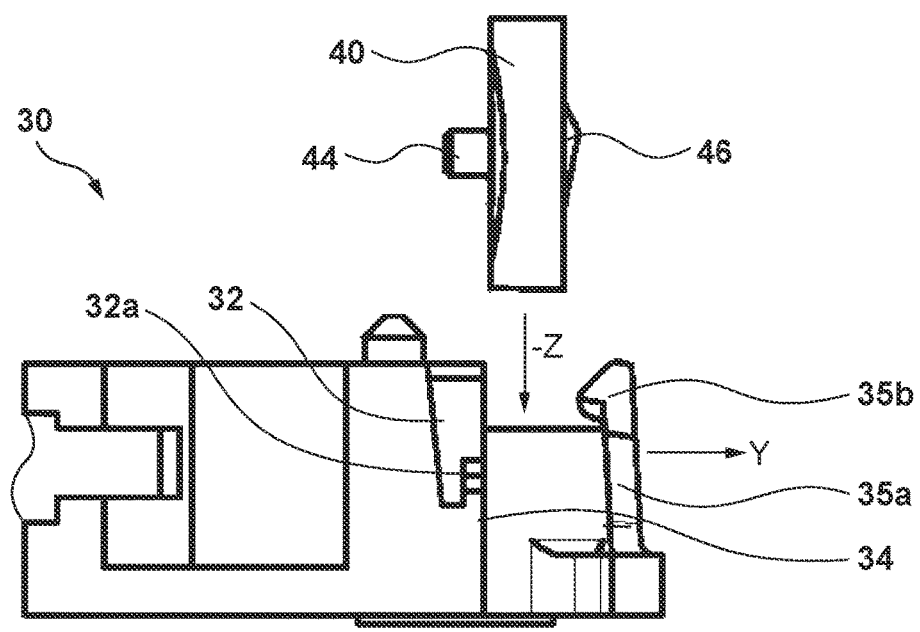
FIGS. 7A and 7B are views illustrating a clamping method of the spectral optical element
Figure 7B:
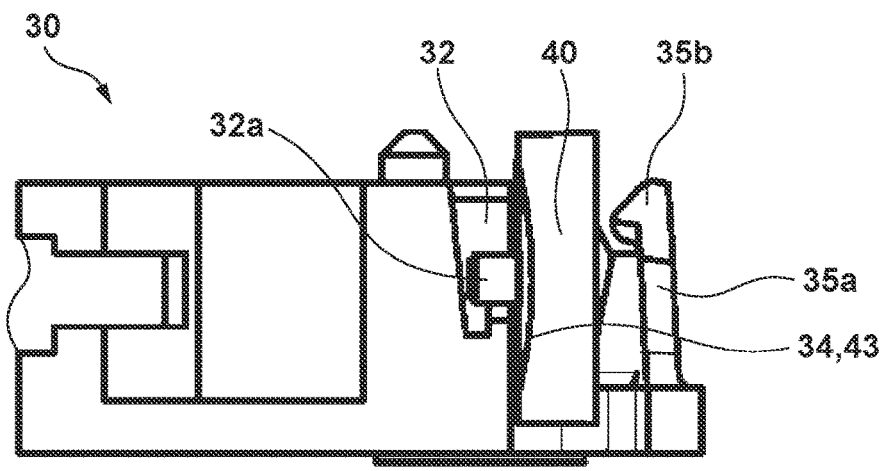
Figure 8A:
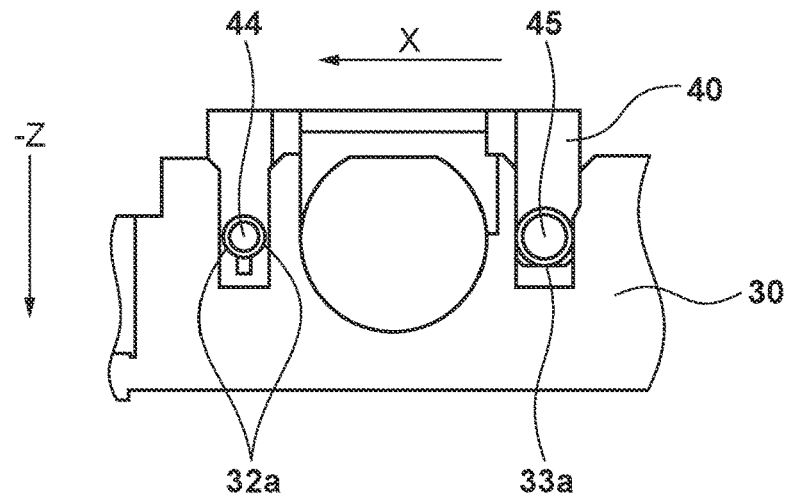
FIGS. 8A and 8B are views for describing an alignment of the spectral optical element
Figure 8B:
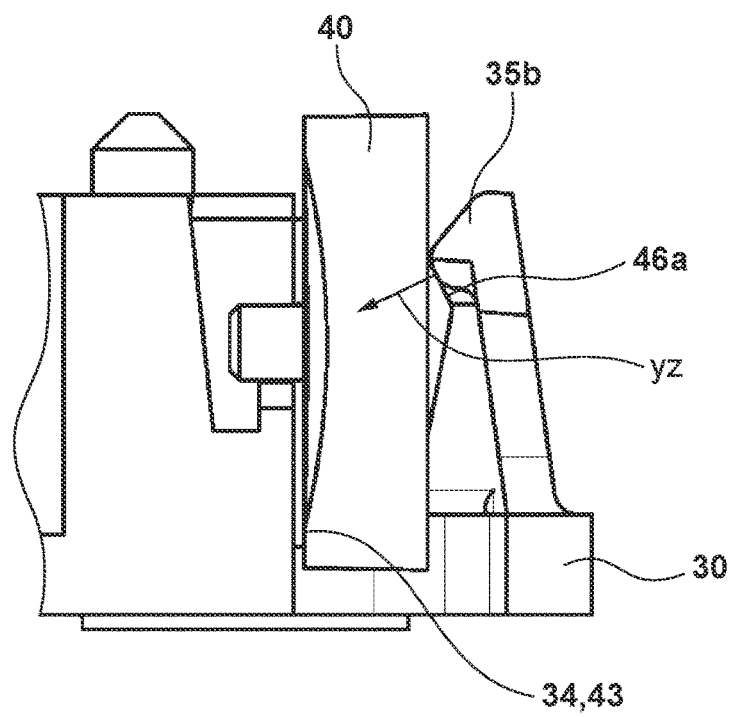

FIG. 7A is a view illustrating a state prior to the spectral optical element 40 being inserted into the attaching portion of the housing 30. FIG. 7B is a view illustrating a state after the spectral optical element 40 is inserted into the attaching portion of the housing 30. FIG. 8A is a view illustrating a state after the spectral optical element 40 is inserted into the attaching portion of the housing 30. This is a view when viewing the outside wall from the inside of the housing 30. FIG. 8B is a view illustrating a state after the spectral optical element 40 is inserted into the attaching portion of the housing 30. This is a perspective view when viewing in the X direction from the side surface of the housing 30.

The spectral optical element 40 is pushed in the −Z direction as FIG. 7A illustrates. By this, the spectral optical element 40 is inserted in a space (attaching portion) between the arm portion 35a and the wall surfaces 34 on the outside of the second side wall 55. At that time, the arm portion 35a of the housing 30 may be pressed by a jig or the like in the −Y direction. Insertion of the spectral optical element 40 becomes easy because the space is widened by this. Configuration may be such that the arm portion 35a is not be pressed in the −Y direction. In such a case, when the spectral optical element 40 is inserted in the −Z direction, the protruding portion 35b of the arm portion 35a begins to contact the inclined surface 46b of the guide portions 46 of the spectral optical element 40. The arm portion 35a gradually deforms by being pressed to the inclined surface 46b because the inclined surface 46b has a slope as FIG. 7A illustrates. The amount of deformation of the arm portion 35a is largest at the connecting portion of the inclined surface 46a and the inclined surface 46b. However, the amount of deformation is designed in consideration as to not reduce the mechanical strength of the arm portion 35a.

The spectral optical element 40 is inserted in the −Z direction until the spectral optical element 40 contacts the housing 30 as FIG. 7B and FIG. 8A illustrate. The first pin 44 and the second pin 45 are cylinders of differing diameters in FIG. 8A. The width of the first groove portion 32 corresponds to the diameter of the first pin 44 and the width of the second groove portion 33 corresponds to the diameter of the second pin 45. By this, it becomes possible to prevent an incorrect insertion (being inserted upside down) of the spectral optical element 40 and it becomes possible to correctly disperse the light beam.

The side surface of the first pin 44 of the spectral optical element 40 contacts the two faces of the V-shaped surface (bottom portion 32a) of the housing 30. By this, the spectral optical element 40 is aligned in the Z direction and the X direction. The side surface of the second pin 45 contacts to the bottom portion 33a of the housing 30. This is useful since the spectral optical element 40 is aligned in the Z direction. Note, the side surface of the second pin 45 may contact or engage the two side walls of the second groove portion 33. In this way, the side wall of the second groove portion 33 may contribute to the alignment of the spectral optical element 40 in the X direction. The cross-sectional shape of the bottom surface of the first groove portion 32 is not required to be V-shaped. The bottom surface of the first groove portion 32 may have a surface contacting from approximately the X direction and a surface contacting from approximately the −X direction to the side surface of the first pin 44.

The protruding portion 35b contacts a portion whose −Y direction height is low in the inclined surface 46a in a state in which insertion of the spectral optical element 40 has completed as FIG. 8B illustrates. Accordingly, the deformation of the arm portion 35a is released. The protruding portion 35b presses the spectral optical element 40 in the direction that an arrow symbol yz indicates. In other words, the protruding portion 35b presses the spectral optical element 40 in the Y direction and the −Z direction. By this, the wall surfaces 34 arranged on the second side wall 55 and the wall surfaces 43 arranged on the front surface of the spectral optical element 40 contact and the spectral optical element 40 is aligned in the Y direction. In this way, although the pressing force added from the arm portion 35a to the spectral optical element 40 includes a Y direction component and a −Z direction component, it does not include an X direction component. In other words, an external force of the X direction is not added directly to the spectral reflective surface 42. Generally, when the spectral reflective surface 42 is deformed, a grid interval of the diffraction grating 47 deviates from the interval envisioned in the design. In other words, the designed dispersion capability is not achieved. In the present embodiment, the dispersion capability of the spectral reflective surface 42 is reduced because a fixation method in which an external force in the X direction is added to the spectral optical element 40. Note, the pressing force may be exerted in the X direction if it does not influence the accuracy of the alignment in the X direction of the diffraction grating 47. In other words, it can also be said that the pressing force in the X direction is smaller than the pressing force in the Y direction and the pressing force in the Z direction.

The spectral optical element 40 assembled in the housing 30 can be removed from the housing 30 by applying pressure to the leading edge of the arm portion 35a in the −Y direction. Accordingly, cleaning or replacement of the spectral optical element 40 is simple.

In this way, by virtue of this embodiment, the miniaturization and design freedom of the housing 30 improves because the spectral optical element 40 is fixed to the outside wall surface of the housing 30. Also, the spectral optical element 40 is fixed by the arm portion 35a integrally formed to the housing 30. Accordingly, it is possible to cause a reduction of the manufacturing cost in forming the arm portion 35a. Also, in addition to being able reduce the manufacturing cost, replacement and the like is simple because a fixture such as an adhesive material or a screw is not necessary. A cost for alignment can also be reduced because the spectral optical element 40 is aligned by contacting a V-shaped surface or a bottom surface formed in the housing 30. No external force acts to fix the spectral optical element 40 in the direction (dispersion direction) in which the diffraction grating 47 of the spectral optical element 40 is continuously formed. Accordingly, the spectral reflective surface 42 becomes less likely to deform and the dispersion capability is maintained.

SUMMARY

The light source 51 as described above functions as a light source (example: such as an LED) that irradiates light onto the surface to be detected of the detection object 100. The light-guiding optical element 52 functions as a light-guiding element which guides the light reflected from the surface to be detected. Note, the light-guiding element is optional and is not necessary. The spectral optical element 40 functions as a spectral element that disperses the light that passes through the light-guiding optical element 52 and the light reflected from the surface to be detected. The light receiving element 53 functions as a light receiving element or a detection element that detects the light dispersed by the spectral optical element 40. The substrate 60 is a printed circuit board on which the light receiving element 53 is mounted. The housing 30 has the first side wall 54 on which the substrate 60 is fixed and the second side wall 55 on which the spectral optical element 40 is fixed. The housing 30 has the arm portion 35a arranged in a position opposite the second side wall 55 so as to pinch the spectral optical element 40 with the second side wall 55 as FIG. 4B and FIG. 8B illustrate. In this way, the spectral optical element 40 is pinched and fixed by the arm portion 35a and the outside wall surface of the housing 30. In this way, it becomes possible to align the spectral optical element 40 with good accuracy by using the outside wall surface of the housing 30. Also, an adhesive or screw ceases to be necessary and assembly becomes simple by employing fixation by pinching by the arm portion 35a. Accordingly, a simple to assemble spectral colorimetric apparatus 20 in which the spectral optical element 40 can be aligned with good accuracy is provided.

The arm portion 35a presses the spectral optical element 40 to the second side wall 55 without pressing the spectral optical element 40 in the dispersion direction (X direction) in which the spectral optical element 40 disperses the light beam as described using FIG. 8B. For example, the dispersion direction (X direction) in which the spectral optical element 40 disperses light is one example of a first direction.

The height direction (Z direction) of the spectral optical element 40 is one example of a second direction perpendicular to the first direction. The Y direction is one example of a third direction perpendicular to the first direction and the second direction. The arm portion 35a functions as a pressing portion that presses the spectral element in the second direction and the third direction. Accordingly, a fixation method of the spectral optical element 40 that tends not to invite a reduction in the dispersion capability of the spectral optical element 40 is realized.

The second side wall 55 may have the first groove portion 32 for aligning the spectral optical element 40 in the dispersion direction as described using FIG. 5A and the like. The spectral optical element 40 may have the first pin 44 which engages with the first groove portion 32. The spectral optical element 40 is aligned in the dispersion direction by the first pin 44 engaging with the first groove portion 32. In this way, the spectral optical element 40 may be aligned in the dispersion direction by the first groove portion 32 and the first pin 44.

The first groove portion 32 contacts the first pin 44 as described using FIG. 8A and the like. Also, the first groove portion 32 may have a bottom portion for aligning the spectral optical element 40 in the height direction (Z direction) perpendicular to the light axis (Y direction) of the light beam that is incident on the spectral optical element 40 and also perpendicular to dispersion direction (X direction). The cross-sectional shape of the bottom portion of the first groove portion 32 may be V-shaped as FIG. 8A illustrates. By this, the first pin 44 becomes difficult to move for not only the X direction but also the −X direction and is aligned with good accuracy because it contacts the two faces of the V-shaped surface (bottom portion 32a).

The second side wall 55 may have the second groove portion 33 for aligning the spectral optical element 40 in the dispersion direction or the height direction as described using FIG. 8A and the like. The spectral optical element 40 may have the second pin 45 which engages with the second groove portion 33. The spectral optical element 40 is aligned in the dispersion direction and the height direction by the second pin 45 engaging with the second groove portion 33. In particular, accurate alignment of the spectral optical element 40 may be further increased by using a plurality of pins such as the first pin 44 and the second pin 45. Also, each side wall of the first groove portion 32 and the second groove portion 33 may be useful as a guide when the spectral optical element 40 is inserted in the housing 30. In other words, assembly may become simple.

The second groove portion 33 contacts the second pin 45. The second groove portion 33 may have the bottom portion 33a for aligning the spectral optical element 40 in the height direction perpendicular to the light axis of the light beam that is incident on the spectral optical element 40 and also perpendicular to the dispersion direction. In this way, the spectral optical element 40 may be aligned in the Z direction by the second groove portion 33 and the second pin 45. The bottom portion 33a of the second groove portion 33 may be a cross-sectional shape or a V-shape. By this, the bottom portion 33a supports the second pin 45 from the X direction and the −X direction and the spectral optical element 40 becomes difficult to move in not only the X direction but also the −X direction. The thickness of the first pin 44 and the thickness of the second pin 45 may differ as described using FIG. 8A. This is useful in preventing an incorrect insertion of the spectral optical element 40.

Note, the positions (left and right) of the first pin 44 and the second pin 45 that sandwich the light axis may be the opposite of the positions illustrated. Although the shapes of the first pin 44 and the second pin 45 are described as columnar, it should be sufficient if the shape can engage with a groove, such as a prismatic column, a cone, or a half sphere. Also, the groove may be a hole in which a protruding body such as a cone or a half sphere is accommodated.

The arm portion 35a may have an elasticity as described in relation to FIG. 7A and the like. The arm portion 35a presses the back surface of the spectral optical element 40 so that the front surface of the spectral optical element 40 contacts the second side wall 55. By this, the spectral optical element 40 becomes easier to align in the optical axis direction (Y direction) of the light beam that is incident on the spectral optical element 40. The arm portion 35a may be integrated into the housing 30. This may be useful in reducing the manufacturing cost. Also, the arm portion 35a may be a member extending from the bottom surface of the housing 30. The guide portions 46 may be arranged on the back surface of the spectral optical element 40 as described using FIG. 6B and the like. The guide portions 46 protrude from the back surface of the spectral optical element 40, contact the arm portion 35a, and function as pressed parts that experience a pressing force from the arm portion 35a. Note, the normal direction of the inclined surface 46a of the guide portions 46 may be parallel to the direction in which the pressing force by the arm portion 35a acts. Also, a contact surface that contacts the inclined surface 46a, in the end portion of the arm portion 35a, may be parallel to the inclined surface 46a. By this, the spectral optical element 40 may become difficult to move in the Z direction.

An opening 56 through which the light beam dispersed by the spectral optical element 40 passes may be arranged on the first side wall 54 as FIG. 3A illustrates. By this, it may become possible for the substrate 60 to be arranged on the outer face of the first side wall 54. This improves the ease of the assembly of the substrate 60 in relation to the housing 30.

The opening 57 through which the light beam that is incident on the spectral optical element 40 passes may be arranged on the second side wall 55 as FIG. 4A illustrates. By this, it becomes possible to arrange the spectral optical element 40 on the outer face of the second side wall 55.

The cover 70 opposes the bottom surface of the housing 30 and is a cap member fixed to the housing 30 as FIG. 2 illustrates. The light beam reflected on the detection object 100 enters the light-guiding optical element 52, is propagated through the interior thereof and is emitted. The emitted light beam propagates in the second space 59 surrounded by the bottom surface of the housing 30, the cover 70, the first side wall 54, and the second side wall 55, and is incident on the spectral optical element 40. A light beam that is dispersed by the spectral optical element 40 also propagates through the second space 59 and is incident on the light receiving element 53. In this way, it may become difficult for foreign particles to intrude into the light path because the light path is sealed. In particular, it may become difficult for foreign particles to adhere to the diffraction grating of the spectral optical element 40.

The detection object 100 having the surface to be detected may be conveyed parallel to the cover 70 as described in relation to FIG. 3A. The spectral optical element 40 may have a concave shape diffraction grating 47. The arm portion 35a may be tilted in relation to a normal direction (Z direction) of the bottom surface of the housing 30 so that it gradually approaches the second side wall 55 from the bottom portion to the leading edge as FIG. 5B and the like illustrate. By this, the pressing force appointed to the elasticity of the arm portion 35a may become easy to maintain.

There may be a plurality of arm portions 35a as FIG. 4B and the like illustrate. By this, it may become possible to hold or support the spectral optical element 40 with good precision.

<Application of the Spectral Colorimetric Apparatus>

Figure 9:
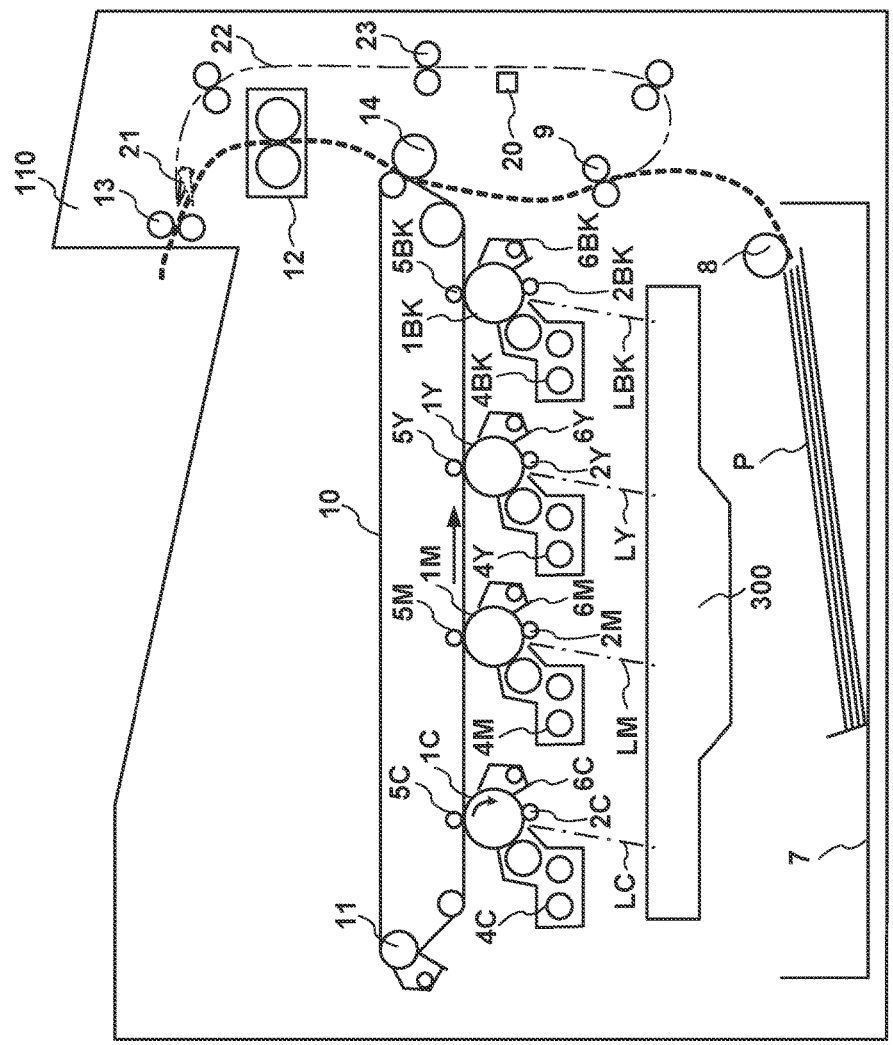
FIG. 9 is a view illustrating an image forming apparatus

FIG. 9 illustrates an image forming apparatus 110 of an intermediate transfer method capable of applying the spectral colorimetric apparatus 20. The image forming apparatus 110 is an image forming apparatus that forms a multicolor image by color mixing a plurality of colorants. Here, although an electrophotographic method is exemplified as an image forming method, another image forming method such as an ink-jet method may be employed. Here, it is assumed that four colors of developers such as yellow (Y), magenta (M), cyan (C), and black (BK) are used. Photosensitive drums 1C, 1M, 1Y, and 1BK are image carriers arranged and evenly spaced respectively. C, M, Y, and BK added to the end of each reference numeral indicates the color of the developer. Primary chargers 2C, 2M, 2Y, and 2BK cause the surface of the photosensitive drums 1C, 1M, 1Y, and 1BK to uniformly charge respectively. An optical scanning apparatus 300 emits light beams (laser beams) LC, LM, LY, and LBK, which are each modulated based on an input image, towards the corresponding photosensitive drums. The light beams (laser beams) LC, LM, LY, and LBK form an electrostatic latent image on the surface of the corresponding photosensitive drums 1C, 1M, 1Y, and 1BK. Developers 4C, 4M, 4Y, and 4BK respectively develop an electrostatic latent image by using cyan, magenta, yellow, and black developers and form a developer image.

A sheet feed roller 8 one at a time feeds a sheet P accommodated in a paper feed tray 7. A registration roller 9 feeds the sheet P synchronized to a write timing of an image toward a secondary transfer unit. Transfer rollers 5C, 5M, 5Y, and 5BK primary transfer a developer image carried on the photosensitive drums 1C, 1M, 1Y, and 1BK to a transfer belt 10. The transfer belt 10 functions as an intermediate transfer body. Cleaners 6C, 6M, 6Y, and 6BK remove residual toner remaining on the photosensitive drums 1C, 1M, 1Y, and 1BK. A driving roller 11 is a roller that causes the transfer belt 10 to rotate. A secondary transfer unit has a secondary transfer roller 14. A multicolor developer image carried on the transfer belt 10 is secondary transferred to a sheet P by the transfer belt 10 and the secondary transfer roller 14 conveying while pinching the sheet P in the secondary transfer unit. After this, the sheets P are conveyed to a fixing device 12. The fixing device 12 adds pressure and heat to the developer image carried on the sheet P and causes it to be fixed. A discharging roller 13 discharges the sheet P on which the image is formed.

As described above, a color mapping table is used in order to reproduce the color tone of an input image in an output image (the image formed on the sheet P). The color mapping table may be called a gamma lookup table for executing a tone correction. There are cases in which the reproducibility of the color tone may be reduced dependent upon on a reduction of the sensitivity of the photosensitive drums 1C, 1M, 1Y, and 1BK, a change of the environment in which the image forming apparatus 110 was installed, or the like. Accordingly, the image forming apparatus 110 forms a test image on a sheet P, the transfer belt 10, or the like, reads the test image by the spectral colorimetric apparatus 20, and generates or updates a color mapping table. By this, the color tone of the input image is reproduced in the output image. Note, a monochrome patch of Y, M, C, and BK respectively may be formed and a monochrome patch of BK and a color mixture patch of Y, M, and C (grey patch) may be formed as the test image for example. Note, BK which is a symbol meaning black may be simply denoted with K.

In the present embodiment, the spectral colorimetric apparatus 20 is arranged on a double-sided conveyance path 22. When a double-sided image formation is designated and a reading of the test image is instructed, a sheet P is sent to the double-sided conveyance path 22. The discharging roller 13 conveys a sheet P on which a developer is fixed in the fixing device 12 in a discharge direction. When the trailing edge of the sheet P passes a flapper 21, the flapper 21 moves from a position indicated by a solid line to a position indicated by a dashed line. The discharging roller 13 starts a reverse rotation and sends the sheet P to the double-sided conveyance path 22. A conveyance roller 23 arranged in the double-sided conveyance path 22 sends the sheet P to the registration roller 9. By this, the second side of the sheet P, the first side of which an image is formed is made to face the transfer belt 10 and the developer image is secondary transferred on the second side. Note, the spectral colorimetric apparatus 20 arranged in the double-sided conveyance path 22 reads the test image formed on the sheet P.

Figure 10:
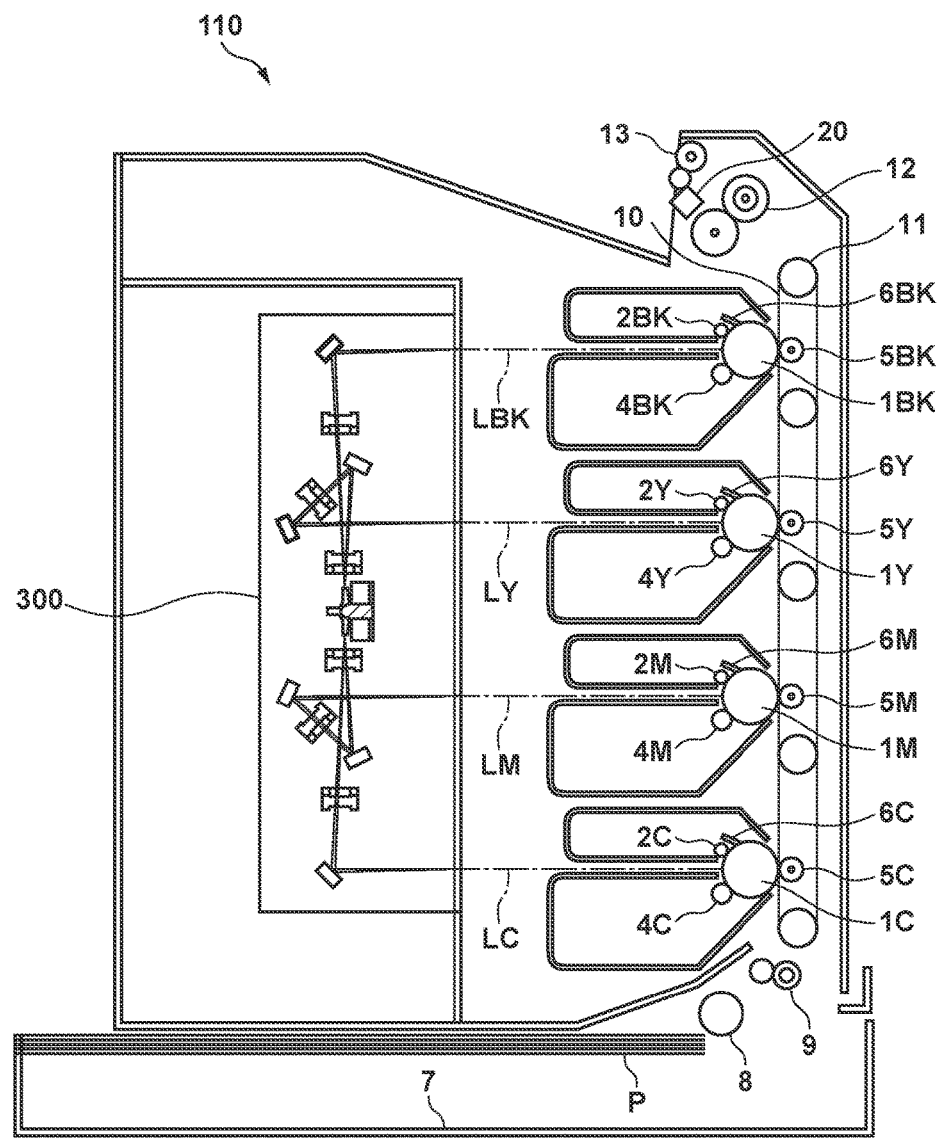
FIG. 10 is a view illustrating an image forming apparatus

FIG. 10 illustrates the image forming apparatus 110 of a direct transfer method capable of applying the spectral colorimetric apparatus 20. The transfer belt 10 of a direct transfer method functions as a conveyer belt which conveys the sheet P. Transfer rollers 5C, 5M, 5Y, and 5BK transfer a developer image carried on the photosensitive drums 1C, 1M, 1Y, and 1BK to a transfer belt 10 to the conveyed sheet P. After this, a fixing process and the like are performed as described using FIG. 9. Note, the spectral colorimetric apparatus 20 is arranged between the fixing device 12 and the discharging roller 13 in the conveyance path of the sheet P and reads a test image formed on the sheet P.

Figure 11:
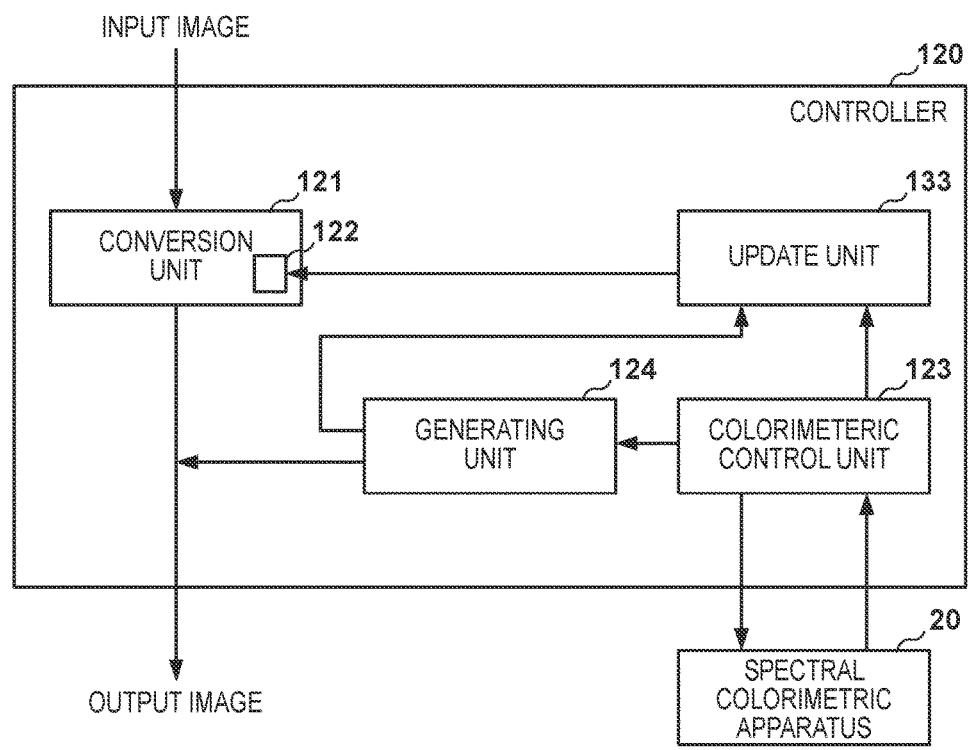
FIG. 11 is a view illustrating a controller of an image forming apparatus.

FIG. 11 illustrates a controller 120 of the image forming apparatus 110. Here, only a function involving reproducibility of a color tone is illustrated. A conversion unit 121 converts the color space of an input image (example: RGB or the like) inputted from a host computer or an image scanner to a YMCK color space. Furthermore, the conversion unit 121 generates Y, M, C, and K image signals (density signals) respectively by converting image data of the YMCK color space by a color mapping table 122 and outputs these to the optical scanning apparatus 300. By this, an output image reproduced from the input image is formed on the sheet P.

As described above, the reproducibility of the color tone is decreased by an environment change or a consumption of a component. A colorimeteric control unit 123 executes an update of the color mapping table 122 when the number of formed images exceeds a predetermined number of sheets for example. The colorimeteric control unit 123 causes an image signal of a test image called a color patch to be generated in a generating unit 124. The generating unit 124 outputs generated YMCK image signals to the optical scanning apparatus 300. By this, the color patch is formed on the sheet P.

The colorimeteric control unit 123 lights the light source 51 of the spectral colorimetric apparatus 20 to illuminate the color patch of the conveyed sheet P. The light receiving element 53 of the spectral colorimetric apparatus 20 outputs a read result of the color patch to the colorimeteric control unit 123. The colorimeteric control unit 123 outputs the read result of the color patch to an update unit 133. The update unit 133 compares the image signals that the generating unit 124 outputted and the read result of the color patch, generates or updates the color mapping table 122 so that the color tone of the color patch is correctly reproduced, and stores it to the storage unit of the conversion unit 121. By this, the color tone of the input image is correctly reproduced in the output image. Note, the color mapping table 122 may be generated for each brand of the sheet P. The color tone of an image changes for each brand because the whiteness level of a sheet P is different for each brand of the sheet P. Accordingly, the color tone is reproduced further with good accuracy by switching the color mapping table 122 for each brand.

In this way, the image forming unit, focused around the photosensitive drums 1C, 1M, 1Y, and 1BK, the controller 120, and the like, functions as an image forming unit that forms an image onto a sheet P. The spectral colorimetric apparatus 20 functions as a spectral colorimetric unit that makes a colorimetric analysis of the colors of an image formed on the sheet P. The update unit 133 functions as a generation unit that generates or updates the color mapping table 122 used by the image forming unit in accordance with a colorimetric result obtained by the spectral colorimetric apparatus 20. Accuracy of the colorimetric result improves because the spectral optical element 40 is aligned with good accuracy as described above. In other words, accuracy of the generation of the color mapping table 122 also may improve and reproducibility of the color tone may improve. In FIG. 10, a direct transfer method in which a toner image is transferred directly to a sheet P from the photosensitive drums 1C, 1M, 1Y, and 1BK is described. However, the present invention can also be employed in an intermediate transfer method in which a toner image is primary transferred from the photosensitive drums 1C, 1M, 1Y, and 1BK to an intermediate transfer belt, and a toner image is secondary transferred from the intermediate transfer belt to a sheet P as illustrated in FIG. 9. In such a case, the spectral colorimetric apparatus 20 performs a colorimetric analysis of a toner image on the sheet P or the intermediate transfer belt.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-081464, filed Apr. 14, 2016, which is hereby incorporated by reference herein in its entirety.

What is claimed is:

1. A spectral colorimetric apparatus comprising:
   a light source configured to irradiate light onto a surface to be detected;
   a spectral optical element configured to disperse reflected light that is reflected from the surface to be detected;
   a light receiver configured to receive light dispersed by the spectral optical element;
   a substrate on which the light receiver is mounted;
   a housing having a first side wall on which the substrate is fixed and a second side wall on which the spectral optical element is fixed; and
   a pressing arm configured to pinch the spectral optical element together with the second side wall and to press the spectral optical element to the second side wall.

2. The spectral colorimetric apparatus according to claim 1,
   wherein the pressing arm is further configured to press the spectral optical element to the second side wall without pressing the spectral optical element in a dispersion direction in which the spectral optical element disperses the light.

3. The spectral colorimetric apparatus according to claim 2,
   wherein the second side wall has a first groove portion that aligns the spectral optical element in the dispersion direction,
   the spectral optical element has a first pin that engages the first groove portion, and
   the spectral optical element is aligned in the dispersion direction by the first pin engaging with the first groove portion.

4. The spectral colorimetric apparatus according to claim 3,
   wherein the first groove portion has a bottom portion that, by contacting the first pin, aligns the spectral optical element in a height direction that is perpendicular to a light axis of light that is incident on the spectral optical element and perpendicular to the dispersion direction.

5. The spectral colorimetric apparatus according to claim 4,
   wherein a cross-sectional shape of the bottom portion of the first groove portion is V-shaped.

6. The spectral colorimetric apparatus according to claim 3,
   wherein the second side wall has a second groove portion that aligns the spectral optical element in the dispersion direction,
   the spectral optical element has a second pin that engages the second groove portion, and
   the spectral optical element is aligned in the dispersion direction by the second pin engaging the second groove portion.

7. The spectral colorimetric apparatus according to claim 6,
   wherein the second groove portion has a bottom portion that, by contacting the second pin, aligns the spectral optical element in a height direction that is perpendicular to a light axis of light that is incident on the spectral optical element and perpendicular to the dispersion direction.

8. The spectral colorimetric apparatus according to claim 7,
   wherein a cross-sectional shape of the bottom portion of the second groove portion is V-shaped.

9. The spectral colorimetric apparatus according to claim 6,
   wherein a thickness of the first pin and a thickness of the second pin differ.

10. The spectral colorimetric apparatus according to claim 1,
    wherein from among a first direction which is a dispersion direction in which the spectral optical element disperses the light, a second direction which is a height direction of the spectral optical element and that is perpendicular to the first direction, and a third direction that is perpendicular to the first direction and the second direction, the pressing arm is further configured to press the spectral optical element in the second direction and the third direction.

11. The spectral colorimetric apparatus according to claim 1,
    wherein the pressing arm has an elasticity, and aligns the spectral optical element in an optical axis direction of light that is incident on the spectral optical element by pressing a back surface of the spectral optical element so that a front surface of the spectral optical element contacts the second side wall.

12. The spectral colorimetric apparatus according to claim 1,
wherein the pressing arm is integrated with the housing and extends from a bottom surface of the housing.

13. The spectral colorimetric apparatus according to claim 1,
wherein a pressed part is arranged on a back surface of the spectral optical element, protrudes from the back surface, and receives a pressing force from the pressing arm when contacting the pressing arm.

14. The spectral colorimetric apparatus according to claim 1,
wherein an opening through which light dispersed by the spectral optical element passes is arranged in the first side wall.

15. The spectral colorimetric apparatus according to claim 1,
wherein an opening through which light incident on the spectral optical element passes is arranged in the second side wall.

16. The spectral colorimetric apparatus according to claim 1, further comprising:
a light-guiding optical element configured to guide light reflected from the surface to be detected to the spectral optical element; and
a cover that is opposite to a bottom surface of the housing and fixed to the housing,
wherein light emitted from the light-guiding optical element propagates in a space surrounded by the bottom surface of the housing, the cover, the first side wall, and the second side wall and is incident on the spectral optical element, and also light dispersed by the spectral optical element propagates in the space and is incident on the light receiver.

17. The spectral colorimetric apparatus according to claim 16, wherein a detection object having the surface to be detected is conveyed parallel to the cover.

18. The spectral colorimetric apparatus according to claim 1, wherein the spectral optical element has a concave shape diffraction grating.

19. The spectral colorimetric apparatus according to claim 1, wherein the pressing arm tilts in relation to a normal direction of a bottom surface of the housing so that it gradually approaches the second side wall from a bottom portion to a leading edge.

20. The spectral colorimetric apparatus according to claim 1, further comprising a plurality of pressing arms.

21. The spectral colorimetric apparatus according to claim 1,
wherein the spectral optical element is pressed by the pressing arm from outside of the housing toward the second side wall.

22. The spectral colorimetric apparatus according to claim 1,
wherein the spectral optical element is detachable from the second side wall.

23. An image forming apparatus comprising:
an image former configured to form a monochrome test image or a color mixture test image on a sheet;
a spectral colorimetric sensor configured to perform a colorimetric analysis on the monochrome test image or the color mixture test image formed on the sheet; and
processor circuitry configured to generate or update a color mapping table used by the image former in accordance with a colorimetric result obtained by the spectral colorimetric sensor,
wherein the spectral colorimetric sensor comprises:
a light source that irradiates light on a surface to be detected of the sheet,
a spectral optical element configured to disperse reflected light that is reflected from the surface to be detected;
a light receiver configured to receive light dispersed by the spectral optical element;
a substrate on which the light receiver is mounted;
a housing having a first side wall on which the substrate is fixed and a second side wall on which the spectral optical element is fixed; and
a pressing arm configured to pinch the spectral optical element together with the second side wall and to press the spectral optical element to the second side wall.

24. A spectral colorimetric apparatus comprising:
a light source configured to irradiate light onto a surface to be detected;
a spectral optical element configured to disperse reflected light from the surface to be detected;
a light receiving element configured to receive light dispersed by the spectral optical element;
a housing having a side wall on which the spectral optical element is provided; and
a presser configured to press the spectral optical element to the side wall so that the spectral optical element is mounted to the side wall.

25. The spectral colorimetric apparatus according to claim 24,
wherein the presser is further configured to press the spectral optical element to the side wall without pressing the spectral optical element in a dispersion direction in which the spectral optical element disperses the light.

26. The spectral colorimetric apparatus according to claim 24,
wherein from among a first direction which is a dispersion direction in which the spectral optical element disperses the light, a second direction which is a height direction of the spectral optical element and that is perpendicular to the first direction, and a third direction that is perpendicular to the first direction and the second direction, the presser is further configured to press the spectral optical element in the second direction and the third direction.

27. The spectral colorimetric apparatus according to claim 26,
wherein the side wall has a first groove portion that aligns the spectral optical element in the dispersion direction,
the spectral optical element has a first pin that engages the first groove portion, and
the spectral optical element is aligned in the dispersion direction by the first pin engaging with the first groove portion.

28. The spectral colorimetric apparatus according to claim 27,
wherein the first groove portion has a bottom portion that, by contacting the first pin, aligns the spectral optical element in a height direction that is perpendicular to a light axis of light that is incident on the spectral optical element and perpendicular to the dispersion direction.

29. The spectral colorimetric apparatus according to claim 27,
wherein the side wall has a second groove portion that aligns the spectral optical element in the dispersion direction, the spectral optical element has a second pin that engages the second groove portion, and the spectral optical element is aligned in the dispersion direction by the second pin engaging the second groove portion.

30. The spectral colorimetric apparatus according to claim 29, wherein the second groove portion has a bottom portion that, by contacting the second pin, aligns the spectral optical element in a height direction that is perpendicular to a light axis of light that is incident on the spectral optical element and perpendicular to the dispersion direction.

31. The spectral colorimetric apparatus according to claim 24, wherein a pressed part is arranged on a back surface of the spectral optical element, protrudes from the back surface, and receives a pressing force from the presser when contacting the presser.

32. The spectral colorimetric apparatus according to claim 24, wherein an opening through which light incident on the spectral optical element passes is arranged in the side wall.

33. The spectral colorimetric apparatus according to claim 24, wherein the spectral optical element is pressed by the presser from outside of the housing toward the side wall.

34. The spectral colorimetric apparatus according to claim 24, wherein the spectral optical element is detachable from the side wall.

35. An image forming apparatus comprising:

an image former configured to form a monochrome test image or a color mixture test image on a sheet;

a spectral colorimetric sensor configured to perform a colorimetric analysis on the monochrome test image or the color mixture test image formed on the sheet; and processor circuitry configured to generate or update a color mapping table used by the image former in accordance with a colorimetric result obtained by the spectral colorimetric sensor, wherein the spectral colorimetric sensor comprises:
  a light source configured to irradiate light onto a surface to be detected;
  a spectral optical element configured to disperse reflected light from the surface to be detected;
  a light receiving element configured to receive light dispersed by the spectral optical element;
  a housing having a side wall on which the spectral optical element is provided; and
  a presser configured to press the spectral optical element to the side wall so that the spectral optical element is mounted to the side wall.

* * * * *